US009999532B2

(12) United States Patent
Mische

(10) Patent No.: US 9,999,532 B2
(45) Date of Patent: Jun. 19, 2018

(54) METHODS AND DEVICES FOR TREATING OBESITY, INCONTINENCE, AND NEUROLOGICAL AND PHYSIOLOGICAL DISORDERS

(71) Applicant: Hans Mische, Grey Eagle, MN (US)

(72) Inventor: Hans Mische, Grey Eagle, MN (US)

(*) Notice: Subject to any disclaimer, the term of this patent is extended or adjusted under 35 U.S.C. 154(b) by 6 days.

(21) Appl. No.: 15/010,863

(22) Filed: Jan. 29, 2016

(65) Prior Publication Data

US 2016/0158051 A1 Jun. 9, 2016

Related U.S. Application Data

(63) Continuation of application No. 11/986,939, filed on Nov. 26, 2007, now abandoned.

(51) Int. Cl.
| | |
|---|---|
| A61M 29/00 | (2006.01) |
| A61F 5/00 | (2006.01) |
| A61F 2/24 | (2006.01) |
| A61M 25/00 | (2006.01) |
| A61M 25/10 | (2013.01) |
| A61M 29/02 | (2006.01) |
| A61F 2/00 | (2006.01) |
| A61B 17/3207 | (2006.01) |
| A61B 17/00 | (2006.01) |
| A61B 17/29 | (2006.01) |
| A61B 17/3209 | (2006.01) |
| A61B 18/00 | (2006.01) |
| A61F 2/88 | (2006.01) |
| A61F 2/90 | (2013.01) |
| A61N 1/36 | (2006.01) |

(52) U.S. Cl.
CPC .......... *A61F 5/0026* (2013.01); *A61F 2/0004* (2013.01); *A61F 2/2493* (2013.01); *A61F 5/003* (2013.01); *A61F 5/0036* (2013.01); *A61F 5/0089* (2013.01); *A61M 25/0069* (2013.01); *A61M 25/10* (2013.01); *A61M 29/02* (2013.01); *A61N 1/36082* (2013.01); *A61B 17/320725* (2013.01); *A61B 2017/00247* (2013.01); *A61B 2017/00256* (2013.01); *A61B 2017/2945* (2013.01); *A61B 2017/32096* (2013.01); *A61B 2018/00392* (2013.01); *A61F 2/88* (2013.01); *A61F 2/90* (2013.01); *A61M 2210/0693* (2013.01); *A61N 1/36017* (2013.01); *A61N 1/36025* (2013.01)

(58) Field of Classification Search
CPC .... A61F 5/0026; A61F 5/0089; A61F 2/0004; A61F 5/003; A61F 5/0036; A61F 2/2493; A61M 25/0069; A61M 25/10; A61M 29/02; A61N 1/36082
See application file for complete search history.

(56) References Cited

U.S. PATENT DOCUMENTS

| | | | |
|---|---|---|---|
| 4,607,618 | A | 8/1986 | Angelchik |
| 5,188,104 | A | 2/1993 | Wernicke et al. |
| 5,330,481 | A | 7/1994 | Hood et al. |
| 5,603,720 | A | 2/1997 | Kieturakis |

(Continued)

*Primary Examiner* — Richard Louis
(74) *Attorney, Agent, or Firm* — Tysver Beck Evans, PLLC

(57) ABSTRACT

Methods and devices are disclosed that provide therapeutic benefit and treatment for a variety of neurologic and physiologic conditions that include obesity, urinary incontinence, and sensory system disorders.

12 Claims, 10 Drawing Sheets

(56) References Cited

U.S. PATENT DOCUMENTS

| | | | |
|---|---|---|---|
| 6,129,685 | A | 10/2000 | Howard, III |
| 6,330,481 | B1 | 12/2001 | Van Wijk et al. |
| 6,540,789 | B1 | 4/2003 | Silvermann et al. |
| 6,764,498 | B2 | 7/2004 | Mische |
| 7,300,449 | B2 | 11/2007 | Mische |
| 2003/0055467 | A1 | 3/2003 | Ben-Haim et al. |
| 2003/0074039 | A1 | 4/2003 | Puskas |
| 2004/0089313 | A1 | 5/2004 | Utley et al. |
| 2004/0158272 | A1 | 8/2004 | Hofle et al. |
| 2004/0167583 | A1* | 8/2004 | Knudson .................. A61N 1/05 607/40 |
| 2004/0172088 | A1 | 9/2004 | Knudson et al. |
| 2004/0181178 | A1 | 9/2004 | Aldrich et al. |
| 2004/0215180 | A1 | 10/2004 | Starkebaum et al. |
| 2005/0154274 | A1* | 7/2005 | Jarsaillon .............. A61F 5/0066 600/407 |
| 2005/0245957 | A1 | 11/2005 | Starkebaum et al. |
| 2005/0261712 | A1* | 11/2005 | Balbierz .......... A61B 17/12009 606/153 |
| 2006/0025808 | A1* | 2/2006 | Thompson ......... A61B 17/3478 606/204 |
| 2006/0089571 | A1* | 4/2006 | Gertner .............. A61B 17/0401 600/593 |
| 2006/0247719 | A1 | 11/2006 | Maschino et al. |
| 2008/0097487 | A1 | 4/2008 | Pool et al. |
| 2008/0275424 | A1* | 11/2008 | Doshi ................... A61B 18/04 604/506 |

\* cited by examiner

METHODS AND DEVICES FOR TREATING OBESITY, INCONTINENCE, AND NEUROLOGICAL AND PHYSIOLOGICAL DISORDERS

CROSS REFERENCE TO RELATED APPLICATIONS

This application is a continuation of application Ser. No. 11/986,939 filed Nov. 26, 2007, the disclosure of which is incorporated by reference in its entirety. Application Ser. No. 11/986,939 is a continuation-in-part of application Ser. No. 09/457,971 filed Dec. 9, 1999, now U.S. Pat. No. 6,375,666; application Ser. No. 10/056,323 filed Jan. 24, 2002, now U.S. Pat. No. 6,764,498; application Ser. No. 10/843,828 filed on May 11, 2004, application Ser. No. 11/602,714 filed on Nov. 21, 2006, application Ser. No. 11/504,514 filed on Aug. 14, 2006. In addition, this application claims the benefit of, and incorporates by reference the following applications: provisional application with Ser. No. 60/727,446 filed on Oct. 17, 2005, provisional application with Ser. No. 60/708,357 filed on Aug. 15, 2005, provisional application with Ser. No. 60/738,892, filed Nov. 22, 2005, and provisional Ser. No. 60/171,687 filed on Dec. 21, 1999, utility application with Ser. No. 09/733,775 filed on Dec. 8, 2000, and utility application with Ser. No. 09/444,273 filed on Nov. 19, 1999, and provisional applications with Ser. Nos. 60/169,778; 60/181,651; 60/191,664; 60/181,445; 60/171,760 and 60/183,706.

FIELD OF INVENTION

The present invention relates generally to the modification of electrical conduction properties within the body for therapeutic purposes. The device and methods are disclosed in the context of treating neurological and physiological disorders that affect a variety of anatomical organs and tissues.

BACKGROUND OF THE INVENTION

The current methods of treating a range of neurological and physiological disorders include the use of systemic drugs, surgical procedures, tissue ablation, electrical stimulation and gene treatments. Many of these disorders are manifested by gross conduction defects or nervous system dysfunction. These neurological disorders are may affect many types of anatomical organs and tissues such as brain, heart, muscle, nerves and organ tissues.

SUMMARY

In contrast to the prior art, the present invention proposes treatment of neurological disorders by subjecting selected tissues to localized mechanical stress. It is difficult to quantify the level of stress applied to the tissue; operable values will vary from low levels to high levels dependent on the type and location of tissue to be treated. The tissues treated can be of many types within the body such as the brain, heart, muscles, nerves or organs.

The invention is disclosed in the context of neurological disorders but other the inventive technology can also be used to treat a wide variety of organs and anatomical tissues, and the treatments of other types of ailments are contemplated as well. For example, other applications of this invention include placement in the pituitary, thyroid, and adrenal glands or in a variety of organs. In addition, placement of the inventive device in tumors may suppress growth due to nerve and vascular compression. The later may prevent blood-born metastasis to other parts of the body. Likewise, hemorrhaging can be stopped or reduced by vascular compression using the invention. Pain management in all parts of the body can be achieved by placement of the inventive device adjacent to selected nerves. Positioning an inventive stress-inducing device within the bone can accelerate healing of broken bones. Disclosure of this invention for neurological and neuromuscular applications is intended to be illustrative and not limiting.

In the treatment of treating cardiac arrhythmias, sometimes the result of a neuromuscular disorder, the inventive device can be positioned within, on, through, or adjacent to heart tissue in order to affect or block electrical conductions that cause symptoms such as atrial fibrillation, pacing defects, hypotension and hypertension. The inventive devices and methods can replace the current practice of RF ablation, surgical procedures (such as the Maze procedure) and anti-arrhythmia drugs.

Proper shape, geometry, and placement of the devices can result in treating the tissue in a similar shape and fashion as those in the aforementioned treatments. The shape of the treatment of the typical Maze procedure can be replicated with the proper physical shape and placement of the inventive device. One embodiment of a device for a method of treating cardiac arrhythmia is a device similar to a rivet. The first end of the rivet would pass through the desired location of the myocardium and be positioned or seated on the external or internal surface, depending on approach. The second end of the rivet combination would be slid along the shaft of the rivet and seated on the opposite side of the myocardium as the first end of the rivet. The first and second end would then be advance towards each other resulting in compression, elongation or mechanical stressing of the myocardial tissue between and proximate to the rivet. The amount of mechanical stressing would be controlled by the distance form the first end to the second end.

The inventive devices and methods can be used in the treatment of cardiomyopathy. A primary cause of cardiomyopathy is a lack of the proteins dystrophin and collagen, the same protein deficiency that exists in the skeletal muscles and leads to generalized weakness, wasting and respiratory complications. Dystrophin and collagen is also needed by cardiac muscle, and its lack can lead to the loss of cardiac muscle cells under the stress of constant contraction. It is know that mechanical forces on tissues can generate increased deposition of collagen fibers within muscular tissues and strengthen these tissues. In the treatment of cardiomyopathy, the inventive devices can provide methods of selectively, broadly or focally, generating mechanical stresses that result in the therapeutic deposition or increased formation of collagen fibers. These fibers can then strengthen myocardial tissues muscle and retard or reversing the effects of cardiomyopathy. This phenomenon can also be used to treat other diseases and illnesses that affect tissue strength and connective tissue orientation, density and volume. In addition, the deposition or formation of collagen in a predetermined formation or matrix can allow of nerve growth along the collagen fibers. This can be useful in forming circuitry for heart conduction pathways as well as the growth of new nerves to treat spinal injuries or paralysis.

Many neurological disorders are a result of improper conduction of electrical currents in various brain tissues. In the case of Parkinson's disease, the conduction currents in the thalamus tissues become disorganized and cause conditions associated with the disease. Likewise, in epilepsy errant currents cause various levels of seizures. In cases of dystonia, errant currents originate in the basal ganglia. Depression and schizophrenia are associated with various electrochemical defects in other portions of the brain. Also, pain symptoms such as trigeminal neuralgia are associated with multiple sclerosis. Paralysis is normally a condition that results from brain injury, nerve damage, or nerve severing.

The localized stresses generated by the inventive device called a Mechanical Stress Device (MSD), will control, inhibit and direct current conduction by reorienting and/or reorganizing the electrical bias of the neurological tissues. In addition, applications for the MSD include compression of selected nerves in order to control, mediate, or suppress conduction along the nerve fibers and bundles that are associated with certain neurologic disorders. The localized stresses also can affect activate or suppress baroreceptors within arteries, veins, heart tissue and other tissues and organs. Affecting the baroreceptors can allow control of various physiologic functions such as sinus rhythm, sympathetic nervous system, blood pressure, hormonal activity and metabolism as examples. The inventive devices and methods can affect the wall of the carotid sinus, a structure at the bifurcation of the common carotid arteries. This tissue contains stretch receptors that are sensitive to mechanical and electrical forces. These receptors send signals via the carotid sinus nerve to the brain, which in turn regulates the cardiovascular system to maintain normal blood pressure. The proper method of use and placement of the inventive device can manipulate the baroreceptors and achieve regulation of the cardiovascular system in order to control blood pressure levels. For example, when place proximate to the carotid sinus, the MSD will apply localized stresses that modify or modulate the stretch baroreceptors. The MSD can be complemented with electrical properties and features that can provide additional affects to the baroreceptors function.

The MSD can be placed internal or external to arteries and veins in order to achieve desired activation of baroreceptors. MSD can be attached to external body plane; skin.

The MSD can also be utilized as an electrically conductive device that creates an electrical connection or "bridge" between targeted anatomical tissues. This technique may facilitate tissue-to-tissue communication, aid in regenerating nerve connections, or affect the electrical conduction between the SA and AV nodes of the heart to overcome pacing defects. Likewise, an MSD may be placed proximate to the pulmonary vein in order to quell, block or mitigate abhorrent conduction currents that cause atrial fibrillation.

In the case of Parkinson's disease, an MSD is implanted in the tissues proximate to the thalamus and induce localized stresses that cause depolarization of the thalamus tissue and thus eliminate or reduce the symptoms of the disease. In Dystonia, the MSD is positioned proximately to the basal ganglia and disrupts the electrical disturbances associated with this disorder.

The same effect is utilized in the treatment of epilepsy and other tissues when the MSD is installed in the targeted brain tissues. An MSD may be place on or adjacent to the vagus nerve in order to mechanically and or electrically cause stimulation. This stimulation of the vagus nerve can provide therapeutic treatment of epilepsy and depression. In addition, MSD stimulation of the vagal nerve can provide treatment for heart function such as cardiac ventricular output, rhythm, and systemic blood pressure. The devices and methods associated with the MSD can also be utilized in the sinuses and various ventricles of the brain to treat personality disorders such as schizophrenia or depression.

Additionally, migraine headaches and Tourette's Syndrome may be treated with the MSD technology. In general, the methods of the invention guide the placement of the device to ensure a therapeutic effect from the device.

In another application, Vestibular disorders, which may interact with blood pressure and heart rate control, can be treated and controlled. The vestibular system is one source of information about uprightness and the system has an affect on the cardiovascular system. Proper placement and manipulation of the vestibular nerve with one or more of the MSD design embodiments can alleviate or control heart rate and blood pressure, as well as physical balance.

The MSD technology may also be used to affect the neurologic response of the digestive system in order to control appetite, digestion or metabolism. In addition, using the previously invented methods and devices in this and the cross referenced patent and applications by Mische, the MSD technology can be used to treat urge or stress incontinence by affecting nerve conduction and neuromuscular function. Also, the neurological and neuromuscular function of the reproductive system can be treated and controlled by using the MSD technology to modify transport and expression of hormones, sperm, ovum, and fluids.

The MSD can be permanently implanted or used acutely and then removed. Likewise, the device can be fabricated of biodegradable materials that are placed chronically and allowed to biodegrade over time.

The devices and methods can be used alone of in conjunction with other therapies. Examples of electrical therapy with various MSD embodiments are given and they include pacing, depolarization, ablation, and tissue alteration.

MSD devices can be configured so that they deliver treatment on a temporary basis and are then removed or disabled. For example, a device such as in FIG. 7 could be used for a temporary treatment regimen or method. The device would be deployed, positioned, expanded for a period of time and then retracted and removed when desired. It could also be used in conjunction with an electrical stimulator. In another embodiment, the device could be a balloon construction that is inflated for the treatment period and then deflated and removed. Additionally, the balloon construction could also have one or an array of electrodes on the surface, as well be made of electrically conductive polymers. The treatment regimen would cease when desired, or if undesired clinical results are observed. The long term result could be attained when the tissues which caused the negative illness state were "retrained" by the MSD type device and further treatment would not be necessary. Additionally, physical remodeling of the tissue may be the result of a temporary treatment regimen.

In some therapeutic cases it may be beneficial to treat in a method that allows the MSD to be placed at the treatment site and the delivery system is left engaged for a period of time. This period of time could be used to observe, measure the effectiveness of the treatment and/or allow a modification to the treatment parameters during this period of time.

MSD devices can be configured so that upon delivery to the desired location within the tissue or body, they are detached from the delivery device by unscrewing, detent release, release of compression or adhesive, or release of other means of securing the MSD to the delivery device. Other means of securing the MSD to the delivery device includes forceps, graspers, swaging, jamming, wedging, friction, tying, magnetics, electrical discharge, melting, fusing, defusing, grapples, etc.

MSD devices can be configured so as to release a therapeutic substance or drug when activated by external or in situ mechanical, chemical or electrical stimuli. These stimuli can actually be provided and distributed by the treated/malfunctioning tissues or tissues proximate to the treated/malfunctioning tissue. The stimuli can be provided by the tissue from localized spasms originating from tissue, muscle or organs, as well as abhorrent electrical signals or biochemical release generated by the diseased/affected tissues. Delivery of the therapeutic substances could continue until the tissues are inactivated and associated symptoms are thus relieved.

In some clinical cases, it may be necessary to contract a volume of tissues. Instead of a device being therapeutic in its expansive state, it may also provide therapy during volumetric contraction. One example could be a device, similar to FIG. 7, with grapples or hooks that are placed within a brain ventricle. Upon activation, the device could grab the walls of the ventricle and collapse or contract volumetrically. Another embodiment would be a device that is expanded in order to grasp tissue and then retracted to contract, elongate or stretch the tissue in a predetermined direction and stress strain parameters. This invention could be used in other types of ventricles, cavities or openings. This can also be used in solid tissues, bones, and organs. MSD technology can be used to expand ventricles and ducts within brain tissues and organs so as to improve drainage of fluids, relief of tissue-to-tissue interface, and to relieve or improve physiologic pressures within a ventricle, or between a ventricle or duct. For example, an expandable MSD can provide a device technology and a treatment method for opening brain ducts and draining excess CSF from the brain.

MSD's can provide a form of mechanical dilatation of tissue. Means of creating tissue dilatation include dilator tools that are on a shaft with the treatment end having physical features that can be one or more of the following: diametrically tapered, rounded, blunt, inverted, or expansive.

MSD's can provide a substrate for carrying neurons or other biologic compositions. These types of devices can also be used to treat many other types of neurologic or physiologic disorders.

MSD's can use their inherent geometries to prevent migration after placement at the treatment site. Additionally, complementary features can be incorporated to the device so that they do not migrate after placement. These complementary features can include spikes, hooks, sutures, bumps, voids, threads, barbs, inverted wedges, filaments, coarse surfaces, adhesives, etc.

MSD's can be constructed so as to be affected by the change in temperature of the tissues proximate to the treatment sites. In some cases, these temperatures may be a result of abhorrent electrical signals, chemical response or mechanical forces within the tissues proximate of the treatment site. When the temperature changes, the physical properties of the MSD changes, as well as the affects of to the brain (i.e., localized stresses and strains). This can be accomplished by the use of temperature sensitive materials such as Nitinol or bi-metallic structures. Other embodiments may use polymers and metals which change shape when affected by electrical, chemical, light, or mechanical energy.

An MSD can be controlled utilizing thermally, pneumatically, or with magnetostrictive properties of the construct.

An expandable preformed MSD can be shaped appropriately (i.e., trapezoid, rectangular, tubular, conical, curved, etc) in order to bias the therapeutic stresses to tissues and avoid imparting stressed to tissues. A MSD's expansion can be controlled by magnetic coupling to a jack, screw or ratcheting mechanism. An external magnet outside of the body would be manipulated to cause an interaction with the implanted MSD. The external magnet may spin and, via coupling, cause a screw to turn and effect the sizing of the MSD, modifying the stresses imparted to the tissue. Likewise, a miniature motor assembly in the MSD can be used to drive the expansion or contraction of the MSD. The expansion and contraction can be modulated one-time, many times over a period, or at a repetitive frequency that causes sustained or short term vibrations. The motor can be operated by an implantable battery system, utilize a hardwire connection to a generator, coupled inductively or capacitively, or magnetically It has been shown that stress to tissues can result in localized increase of collagen deposits. These collagen deposits can improve tissue strength as well as create a matrix for nerve regeneration. The orientation of stresses created by the MSD devices can predetermine the deposition of collagen and nerves.

This phenomena can be use to reconnect severed nerves or reroute nerves and electrical conduction pathways within tissues such as the brain and heart.

MSD can physically, biologically, mechanically, chemically or electrically modify production of detrimental biochemical/brain chemistry such as dynorphin or a chemical in the brain called CREB or cyclic AMP responsive element binding protein, which can cause depression, anxiety or other maladies. Biological and chemical additives to the MSD can scavenge or modify detrimental biochemical/brain chemistry such as dynorphin that can cause depression or other maladies. Likewise, MSD's can modify the action potential of the brain cellular make-up by reversal of the electrical potential in the plasma membrane of a neuron that occurs when a nerve cell is stimulated; by changing the membrane permeability to sodium and potassium.

MSD technology in the form of a balloon can provide a number of design alternatives and treatment methodologies. For example, a balloon that conforms to the cortical surface of the brain can provided constant or variable localized stresses that provide therapy. The balloon surface could be smooth or flat, or could have projections or bumps that contact the brain tissue in a predetermined fashion. This allows for distinct and focal stresses and strains on brain tissue. The MSD balloon can be controlled by the connection to an implantable pump mechanism. The pump regulates the expansion and deflation of the balloon in order to customize the size and shape of the balloon. This allows for varying levels of stress to the tissue. The pump can be controlled by a wireless remote control via the likes of inductive coupling, RF or Digital communications, etc. Also, the pump could be controlled by hardwire connection to a control module. The pump could be controlled by health care personnel or by the patient. A balloon can be shaped appropriately (i.e., trapezoid, rectangular, tubular, conical, curved, etc) in order to bias the therapeutic stresses to tissues and avoid imparting stressed to tissues.

An MSD can be placed anywhere in the body so that it impacts neurologic tissues and provides therapy. These areas include Area 25 in the brain to aid in treating depression. A MSD can be placed proximate the pudenal nerve to treat incontinence.

All MSD designs can be positioned within tissues in a remote location from the region where an abhorrent signal is originating. In this case, the MSD can interrupt a signal pathway, circuit, or transmission line. For example, an MSD can be placed on the cortical surface of the brain. Placement and stress applied in the proper location can treat/control a number of physiologic functions (i.e., atrial fibrillation, pain, incontinence, blood pressure, hormonal activity, etc). For example, proper placement on the cortical surface can help treat Parkinson's tremors by interrupting or modifying the corto-basal ganglia motor control loop. An MSD may be formed in a Cartesian coordinate fashion so as to be able to program the affect to the tissue in the most desirable fashion.

A MSD can be positioned on the spinal column, spinal nerve or vertebral nerves to block or dissipate abhorrent signals and/or pain in remote regions of the body.

An MSD can be used to treat sciatica by placement directly on the sciatic nerve or in the spinal column nerve bundle. Likewise, scoliosis may be treated by selective treatment of nerves and/or nerve bundles with a MED. Additionally, an MSD can provide treatment of atrial fibrillation by placing a MSD in the proper location of the spinal nerve/bundle column to control the fibrillations A MSD in the form of an expandable Deep Brain Stimulator (DBS) lead can be used to apply controlled stresses, record EEG and other parameters, connect to generator for stimulus. These actions can be done simultaneously, sequentially, or in an order determined by the operator. A MSD in the form of a DBS lead can be used temporarily or implanted permanently. The expansion of the MSD at the tip of the lead can be controlled at the proximal end of the lead by pulling, pushing, twisting, sliding, and mechanisms. The sizing of a MSD can be controlled by power or information provided by a DBS or electrical generator. A separate "communication" channel can be used to send signals or power to the MSD that dictate the expansion, contraction or vibration of the MSD. The generator/MSD configuration would thus provide the ability to treat the patient with complementary effects. An MSD can be configured in such a fashion so as to accept or "dock" with a standard DBS lead. Likewise, it can be configured so as be disengaged or "undocked".

MSD's that pinch neurologic tissues (brain, connective tissues, nerves, muscles, organs, etc) alter the electrical and/or chemical properties. This phenomenon is useful in treating disorders. MSD's can be implanted that electrically or chemically neutralize tissue to treat disorders. The tissues electrical potential can be "grounded" to dissipate the abhorrent signals. The tissues chemical potential can be changed by affecting the pH of certain regions by inserting chemicals, drugs, or elements that modify these regions pH. These substances can be inserted alone or be part of a complex treatment regimen or on a device (permanent implant or temporary implant). An MSD device can also be useful in suppressing or deterring the formation of lesions associated with multiple sclerosis.

The MSD can be a partial or complete band or hoop that goes on or around a portion of the brain or the entire circumference. The MSD may be activated manually through the skull by having a portion of the MSD protruding from the skull bone that is manually activated by the patient or medical personnel. The manually activated portion can be under the scalp or protrude from the scalp.

A MSD can be used to treat ulcer (stomach, intestinal, diabetic, etc) when placed proximate an ulcer and cutting off blood flow and neurologic activity. The MSD can be placed endoscopically or angiographically if needed.

An MSD electrode can be made with moveable sheath that allows controlled exposure of one or more electrode elements as necessary. Exposure may occur by the projection or expansion of the electrode element(s) in a radially, axial, or longitudinal fashion. Electrode construction with multiple barbs that project in a racially and/or longitudinal or axial direction. If desired, barbs/projections can be electrically and mechanically independent from each other. An MSD electrode with a moveable sheath will provide variable exposure and expansion of electrode element. An MSD electrode can be made so that the operable portion is biased in a predetermined radial direction from the axis. The radial direction can encompass from 0 to 360 degrees. In alternative embodiments, there may be a number of elements that are independently controllable in order to customize the electrodes projections and effects.

As discussed in the previously in the applications and patents by Mische and Mische et al that this application claims the benefit of and incorporates by reference, the MSD technology application can be used to treat a number of physiologic disorders and provide therapeutic methods for syndromes. These previous applications and patents teach one skilled in the art the following methods and devices which are being claimed.

Urinary Disorders

One particular application is in the treatment of urinary disorders such as urge urinary incontinence, hyperreflexia of detrusor (over-active bladder), and vesical-sphincter dyssynergia as examples. Urge incontinence is associated with persistent sensation that the person needs to urinate. It causes much discomfort and anxiety for the sufferer. Current treatment regimens include the implantation of neurostimulation devices that connect to the sacral nerve via an electrode, surgical nerve disconnect, drugs, botox injections and capsaicin injections. All of these current treatments result in the prevention or blockage of signal transmission between the bladder nerves and the brain. The neurostimulators create a nerve block that prevents the urge sensation from being transmitted to the brain. One of the problems with the neurostimulator technology is the price, component reliability, electrode failure, battery life, and the implantation of an large electrical generator. Treatments with agents and drugs are not usually a permanent solution. Cutting nerves (e.g. vagotomy) is permanent. The MSD technology can provide an effective nerve block by creating a total or partial mechanical nerve block when placed proximate to the sacral nerve. The block occurs when the MSD imparts creates localized or direct mechanical stress, strain or forces on the target nerve or innervation zone. The mechanical force can result when the nerve or innervation zone is compressed, expanded, elongated as examples. The implantation method can be surgical or endoscopically. Other urinary bladder disorders that may be treated with the inventive method and devices include non-obstructive urinary retention and urgency-frequency. In a preferred procedural embodiment, the MSD would be place adjacent, around, or within the sacral nerve sheath or nerve bundle. The procedural method would preferably include a test sequence in order to identify the appropriate nerve site.

A test stimulation can be applied to the site with electrical stimulation via an electrode or with mechanical stimulation. The device used for test stimulation may in fact be the MSD or a portion of the MSD. When the physician identifies the nerve site, an MSD can then be advanced to the site. An MSD that has an adjustable physical profile can then be either adjusted or left in place for future adjustment. As previously disclosed in the applications and patents that this patent claims benefit to, the MSD may be connected to an electrical generator, incorporate an electrical generator, or be activated by an external electrical generator. For one skilled in the art, it is apparent that other forms of activation or complementary therapies and technologies can be implemented with the MSD and are also incorporated by reference and claim benefit of the previously disclosed applications and patents. The sacral nerve can be accessed near the sacrum either surgically or preferably percutaneously. Sympathetic nerve fibers coming from the hypogastric plexus of nerves or parasympathetic nerves traveling to the bladder with pelvic splanchnic nerves can also be directly affected within the body or near the bladder with surgical techniques or with minimally invasive methods such as laparoscopy. The MSD can be implanted through a needle, catheter or cannula. The MSD can be in many forms as previously described. The MSD may impinge, pinch, clamp, wrap, stretch, elongate, compact, or compress the nerve. The MSD fashioned from biodegradable, bioerodable, or absorbable materials can provide for a predetermined treatment timeframe. This may allow for the "retraining" or "reprogramming" of tissues, organs or the neurologic system and negate or reduce the need for further therapy. The MSD technology may also be used by placing the MSD directly into the bladder and expanding it. The stresses imparted to the bladder wall affects the bladder innervation and relives symptoms of urge and the affects of diseases such as interstitial cystitis. The MSD may be place surgically or introduced through the urethra or through the ureters. The affects may be similar to the outcomes of hydrodistension of the bladder, although the results would last as long as the MSD device is left in the bladder. The MSD for this application can be self-expanding or expanded with a device such as a balloon catheter. The MSD could be further activated by heat, electrical energy, or other methods discussed previous, in order control the expansion or contraction of the device as needed. The MSD could also be applied or wrapped around the outer surface of the bladder.

Eating Disorders

Another embodiment includes the treatment of eating disorders such as obesity and bulimia. In the treatment of obesity, the stomach triggers hunger pangs that are transmitted to the brain telling the person to eat. When the stomach transmits these signals too often, the person eats to often and thus gains weight due to the over consumption of food. Current treatments include stomach surgery to reduce its volume and neurostimulators that stimulate the vagal nerve. In this type of therapy, the neurostimulators again are providing treatment by causing a nerve block. The implant procedure again requires surgery and the implantation of an expensive electrical generator.

The MSD technology can provide an effective nerve block by creating a mechanical nerve block, or down-regulation of the neural activity, when placed proximate to the vagal nerve near the stomach or other organ of the gastrointestinal tract. If so desired, the forces applied to the nerve can be adjusted or predetermined in order to selectively affect the afferent and efferent nerve activity, as well at to generally affect the nerve synapses, neurotransmitters, mechanosensory properties as well as specifically affect the nerves homotropic and heterotropic modulation characteristics. It should be noted that the splanchnic nerve, or splanchnic nerves, may also be the target nerve for MSD application in the treatment of obesity. Therefore, it should be understood by one skilled in the art that the MSD inventions, methods, and devices can be utilized to provide beneficial therapy my manipulation of the splanchnic nerve or other nerves. In fact, the vagal, splanchnic nerve, or other nerves may be targeted at the same time for a combinatory result. Likewise, the celiac ganglia may also be targeted.

The MSD implantation method can be performed surgically or with minimally invasive procedures such as endoscopically or laparoscopically. Although the following describes treating a vagal nerve with an MSD, it is also intended to illustrate the use for other nerve-target applications. In the endoscopic embodiment, the doctor would use many of the same tools to perform the MSD implantation that are currently used for endoscopic procedures. In one embodiment, the doctor would utilize a system comprising of an endoscope and a trocar or hollow needle that pierces the nerve bundle. Once the needle has penetrated the covering, the MSD is then advanced through the needle and proximate the vagal nerve, or within the vagal nerve bundle. Likewise, it can be placed within or adjacent to the nerve and vascular sheaths. It can also be implanted on or within the organs, muscle, and vascular system. The MSD can be a solid, static device that fills a volume or an expandable device. In either case, the MSD imparts mechanical stress to the nerve and results in a blocking of nerve transmission. One or more MSD's can be positioned at varying intervals along or proximate to the nerve. The MSD can have means to anchor in place, Such means can be barbs or tines, The MSD can be connected to an electrical generator or drug pump in order to get complementary therapeutic responses. As previously discussed, the MSD can be in the form of an inflatable balloon that compresses, impinges or stretches nerves in order to create nerve block or down-regulation. The balloon can be made of an elastomeric or a non-compliant material. An elastomeric balloon would allow for varying geometries as the amount of inflation media is injected. Also, the balloon can be readily adjusted as needed to vary the treatment level. As discussed previously, the balloon can be controlled by an internal or external pump. The balloon can also be placed and operated within the gastrointestinal tract. The balloon may also be in a tubular form so as to allow passage of food, fluid and particles through the digestive tract. The MSD can also take place as injectables such a slurry, paste, gel, liquid, foam, or dispersions that are injected within or around the nerve bundles. The injectables can also be loaded with other substances such as Botox, anesthetics (e.g. lidocaine), stimulants, irritants, or other substances that can aid in blocking the nerve conduction. As previously mentioned, the MSD can be made of a biodegradable material that degrades over a prescribe time in order to regulate the time period that the nerve is blocked or down-regulated, and thus regulate the time period of treatment. This inventive method of treatment allows for a therapeutic time-frame that is a function of the biodegradable rate of the MSD. For the sufferers of obesity, the therapeutic timeframe may be of length so that the patient loses a sufficient and healthy amount of weight. This may allow for the person to regain an active and healthy lifestyle that may aid in maintaining a healthy body mass. In another embodiment, the MSD may provide a partial block of vagal nerve function so that the intensity of the nerve signals is reduced. This may minimize the level of hunger that the person experiences thus they may not ingest as much food.

In another embodiment, the method of treatment would include an MSD that is implanted on the stomach and proximate to the vagal nerve. As the stomach expands with food intake, the MSD in pushed, pressed, compresses or elongates the vagal nerve so as to affect the block the conduction, or block, of the nerve. An MSD can be in the form of a "Chinese finger-lock", a braided-tubular structure. This type of structure decreases in diameter as its ends are pulled apart, and expands in diameter as the ends or pushed together. It can then be placed around the vagal nerve on the surface of the stomach and fixated at both ends. As the stomach fills with food and expands, the ends of the MSD structure move apart and its tubular diameter decreases. As it decreases in diameter, the MSD compresses the nerve, creates a nerve block, and subsequently the person feels hunger satiate and reduces or stops eating. This structure can also be made in a scale large enough to fit over a portion of the entire stomach. Again, as the person eats and the stomach fills, the can compress or restrict the stomach and cause satiety of hunger. Using the expansive properties of this type for therapeutic purposes allows it to be placed within an organ such as on the internal wall of the stomach. If the device is attached to the stomach wall, it will expand as a function of the stomachs expansion as food is ingested. Therefore, as the stomach expands, the device expands and exerts force on and through the stomach lining and affecting the innervation of the stomach. This will cause mechanical nerve blocks and provide a sense of satiety to the patient. Again, this device can be made of materials that are biodegradable, bioerodable or digestible so that the therapy is not permanent. The remnants can be pass through the intestinal tract or defecated. Selecting the appropriate materials will allow a for a predetermined treatment timeline. This device can be inserted within the stomach surgically, gastropically, endoscopically or swallowed by the patient. In the embodiment where the device is swallowed, the expanding MSD can be compacted and coated with a restricting material, formed into a pill or inserted into a pill capsule. Upon residing in the stomach, the device would deploy when the coating, pill or capsule disintegrate in the environs of the stomach. As it expands, it conforms to the stomach form. It may be important to have the patient drink enough fluid to expand the stomach prior to swallowing the MSD. Magnetic materials may be a component of the MSD so as to interact with a magnetic device in order to provide the ability to properly orient the swallowed MSD within the stomach. He magnetic device can be operated outside or inside the stomach. The swallowed MSD may also be of the form of a compressed foam material that expands when released. The foam material could be swallowed in similar formats or delivered by other aforementioned methods. As the foam form expands, it would fill a predetermined volume of the stomach and limit food intake, as well as providing downregulation or nerve blocking of the stomachs vagal innervation as it provides mechanical stresses as it expands. The expanding foam material could actually be taken as a supplement before or during meals. In a preferred embodiment, the material could be biodegradable or digestible so that it is not permanently installed. It can follow the digestion schedule of co-ingested food and pass through the intestinal tract with the digested food. The foam material can also have nutritional supplements, medicines, or diagnostic materials as components. Medicines within the foam MSD can be beneficial to locally delivery therapy to stomach ulcers or other alimentary organ maladies. The foam material may be composed of cellulose bases or other materials. The foam MSD may expand or swell when chemically activated by the gastric fluids within the stomach. Another embodiment can use the foam as substantially tubular form that approximates a lining of the stomach. The thickness of this lining can be predetermined. It may also be formed in situ using a delivery system that injects a form around a balloon that is inserted within the stomach. The balloon is then collapsed leaving the formed lining in place. Other methods and devices may be used to create this lining without departing from the inventive intent. This type of lining may also be used to treat nasal sinus disorders while maintaining air flow or to bridge anastomosis (connection) of various organs and biologic conduits. Although the use of the expanding foam MSD form has been discussed for use within the stomach, it is apparent to one skilled in the art and technology that is cal be used to provide treatment to other body organs, orifices, and physiology. It can be inserted or injected in, on or near selected nerves, blood vessels, tracts (i.e, urinary, reproductive, digestive tracts) and biologic structures. Alternative geometries, structure, materials and designs can also be implemented designed in order to achieve similar outcomes. For example, expanded Teflon, similar to that used for vascular grafts, can be used to achieve similar results. Metals, polymers, fabrics, balloon-structures, or combinations of these can be used. The MSD can also be a dissolvable or metabolizable substance or material. The MSD technology can also be used to treat the over-production of acids within the stomach by affecting the conduction of the vagal nerve structure. Too much stomach acid causes ulcers and stomach irritations. In all the cases, the procedure can actually be done in a minimally invasive fashion by accessing the vagal nerve from within the stomach. In this case, gastroscopy could be utilized to access the interior stomach and identify the proper location of the vagal nerve. Once located, the MSD could be advanced in to, or through the stomach, and proximate to the vagal nerve. MSD designs such as a clip, a suture or a loop could embrace and compress the nerve. This method and devices can also be used to treat other organs with examples such as the urinary bladder, liver, prostate, and uterus. In another embodiment, the MSD may be a structure that is inserted within various locations of the gastrointestinal tract and expands against the internal walls of the selected alimentary organ. The force applied to the wall affects the vagal nerves branding into the organ and affects the conduction. In particular embodiment, the MSD can be permanent, biodegradable or digestible. The MSD can extend into the esophagus and intestinal tract if so required. In all of the aforementioned embodiments, the MSD can function as an electrode, or have one or more discrete electrodes incorporated for monitoring, stimulation, or both. In all embodiments, the MSD can be activated or coupled with electromagnetic or magnetic energy from an external source. The source may be directed coupled to the MSD or coupled wirelessly via inductive, capacitive, magnetic and other external energies.

The MSD technology and methods may also be used to treat certain types of fecal incontinence by blocking afferent or efferent nerve conduction between the intestinal tract sphincters and the brain. Although the nerve of choice would again be the sacral nerve, other nerves may also be targeted for the treatment.

As previously disclosed, the MSD can also be designed to react with body fluids in order to generate therapeutic results. In this case, the gastric acids of the gastrointestinal tract can react with the MSD in a therapeutic fashion.

The MSD technology and methods can also be used to prevent vomiting and nausea by affecting the Vagal nerve conduction. This may be beneficial in the treatment of bulimia and self-induced vomiting. The MSD can also be used to block or desensitize the nerves and constrictor muscle within the throat. This would prevent or limit the ability of the person to cause self-induced vomiting. The procedure can be easily performed by inserting or injecting an MSD into the nerves or constrictor muscle via the mouth or nasal sinus. The same type of MSD devices and methods can be used to treat persistent or psychogenic coughing. Again, the MSD can be permanent, temporary or biodegradable.

In an alternative embodiment, the MSD tubular structures can be used to reduce nerve compression when place around the nerve and the MSD expands radially, the pressure is removed from the nerve. Carpal tunnel syndrome may be treated with this method and devices.

As previously disclosed in the applications and patents that this patent claims benefit to, the MSD may be connected to an electrical generator, incorporate an electrical generator, or be activated by an external electrical generator. For one skilled in the art, it is apparent that other forms of activation or complementary therapies and technologies can be implemented with the MSD and are also incorporated by reference and claim benefit of the previously disclosed applications and patents.

Another debilitating neurologic disorder is palmar hyperhidrosis. This disorder causes the sufferer to have sweaty palms. Current treatments are similar to the aforementioned disorders and include a surgical procedure called sympathectomy; cutting of the sympathetic nerve. Another method that is less invasive uses phenol to kill the nerve. Using MSD technology and methods and previously discussed, a permanent or temporary manipulation of the sympathetic nerve may be prove beneficial. Again, the preferred embodiment would include minimally invasive procedures and devices. The placement of the MSD could be guided by imaging technologies such as CT fluoroscopy. One target for implantation on could be proximate of the sympathetic junction at the third vertebra. The MSD) can be in the form of a clip or a device that impinges or pinches the nerve to cause a block. If necessary the procedure can be reversed by simply removing the MSD. Individual sympathetic nerve innervation crossing the second rib level be divided and isolated with the MSD. The Kuntz nerves can be an isolated nerve target for MSD treatment.

Other ailments that may benefits from the MSD technologies ability to block, down-regulate neural activity, inhibit inflammatory processes include pancreatitis, colitis, irritable bowel syndrome, dyspepsia, sciatica, ileus, Crohn's disease, diabetes, dysfunctional valves and sphincters of the alimentary organs, and gastroesophageal reflux disease (GERD) as examples. The enteric nervous system, as whole or portions thereof, may also be manipulated by the MSD technologies. The MSD can also affect the neurologic function and secretion function of the pancreas, liver and gall bladder. In addition to providing therapeutic affects, the MSD technologies may also protect other organs by preventing antidromic responses or to block adverse side effects of the signals from electrical-based neurostimulation, drugs, and other treatments on proximate organs such as coronary, respiratory, adrenal, and others.

As mentioned previously, MSD technology can be used to compress the vascular to control bleeding or hemorrhaging. This is particularly valuable for the treatment of bloody noses. As shown in FIG. 2, the MSD can be in a tubular form and similar to a vascular stent, placed into the nasal and sinus passages, expanded (e.g. self-expanding, balloon-expanded) at the sight of bleeding and causing tamponade of the bleeding vascular tissue. The MSD can coatings such as drugs, minerals, gauze, fabric, lubricants, or other materials that assist in causing hemostasis. A tubular form would allow air passage through the MSD and maintain patient comfort; however other forms can are anticipated. The MSD can also be connected to an RF cautery generator to assist in creating coagulation and hemostasis.

In addition, as FIG. 2 further illustrates and educates one skilled in the art, the MSD devices and methods can also be used for rhinoplasty and septoplasty as well as to treat perforated septum's, sinusitis, and other nasal sinus obstructions. Further support for devices and methods similar to MSD is covered by Mische in the pending U.S. patent application Ser. No. 09/733,775 that claims the benefit of provisional applications with Ser. No. 60/169,778, 60/181, 651 and 60/191,664, which discloses devices and methods for the treatment and support of broken noses and sinus cavities, and which all are hereby incorporated by reference herein.

The MSD technology and methods can treat other neurologic or physiologic disorders such as Tourette's Syndrome, muscle spasms and contraction, nerve compression, nausea, tinnitus, vertigo, Meniere's Disease, Raynaud's Disease, Facial Blushing (erythrophobia), burning face (hyperpyrexia), rosacea, tardive dyskinesia, oropharyngeal and other dysphagia, achalasia, sphincter contractions, pancreatitis, vomiting, persistent or psychogenic cough. The treatment of these diseases is illustrative and is not meant to be limiting. With the foregoing detailed description of the present invention, it has been shown how the objects of the invention have been attained in a preferred manner. Modifications and equivalents of disclosed concepts such as those which might readily occur to one skilled in the art are intended to be included in the scope of the claims which are appended hereto.

BRIEF DESCRIPTION OF THE DRAWINGS

Throughout the several views of the drawings several illustrative embodiments of the invention are disclosed. It should be understood that various modifications of the embodiments might be made without departing from the scope of the invention. Throughout the views identical reference numerals depict equivalent structure wherein.

DETAILED DESCRIPTION

The device and methods, which are similar to those discussed in the patent application with Ser. No. 09/444,273 filed on Nov. 19, 1999 by Mische entitled, "Mechanical Devices for the Treatment of Arrhythmias" which is incorporated by reference herein.

Throughout the description the term mechanical stress device MSD refers to a device that alters the electrical properties or chemical properties of physiologic tissues. The device may be made of metal such as Nitinol or Elgiloy and it may form an electrode for electrical stimulation. One or more electrodes may be associated with it. The MSD may incorporate fiber optics for therapeutic and diagnostic purposes. The device may also be made from a plastic or other non-metallic material. The MSD may also incorporate a covering of polymer or other materials. The MSD may also be a composition of different materials. The MSD may be smooth or have cutting or abrasive surfaces. The MSD may have, but not limited to, other elements that protrude from the contour of the surfaces such as spindles, splines, ribs, points, hooks, wires, needles, strings, and rivets.

The MSD may be implanted for chronic use or for acute use. Biodegradable materials that degrade or dissolve over time may be used to form the MSD. Various coatings may be applied to the MSD including, but not limited to, thrombo-resistant materials, electrically conductive, non-conductive, thermo-luminescent, heparin, radioactive, or biocompatible coatings. Drugs, chemicals, and biologics such as morphine, dopamine, aspirin, lithium, Prozac, genetic materials, and growth factors can be applied to the MSD in order to facilitate treatment. Other types of additives can be applied as required for specific treatments.

Electrically conductive MSDs, or MSDs with electrode elements, may be used with companion pulse generators to deliver stimulation energy to the tissues. This electrical therapy may be used alone or in combination with other therapies to treat the various disorders. Electrical therapies may be supplied from implantable devices or they may be coupled directly to external generators. Coupling between the MSD and external generators can be achieved using technologies such as inductive, capacitive or microwave coupling as examples. The MSD may also be designed of geometries or materials that emit or absorb radioactive energies.

Figure 1:
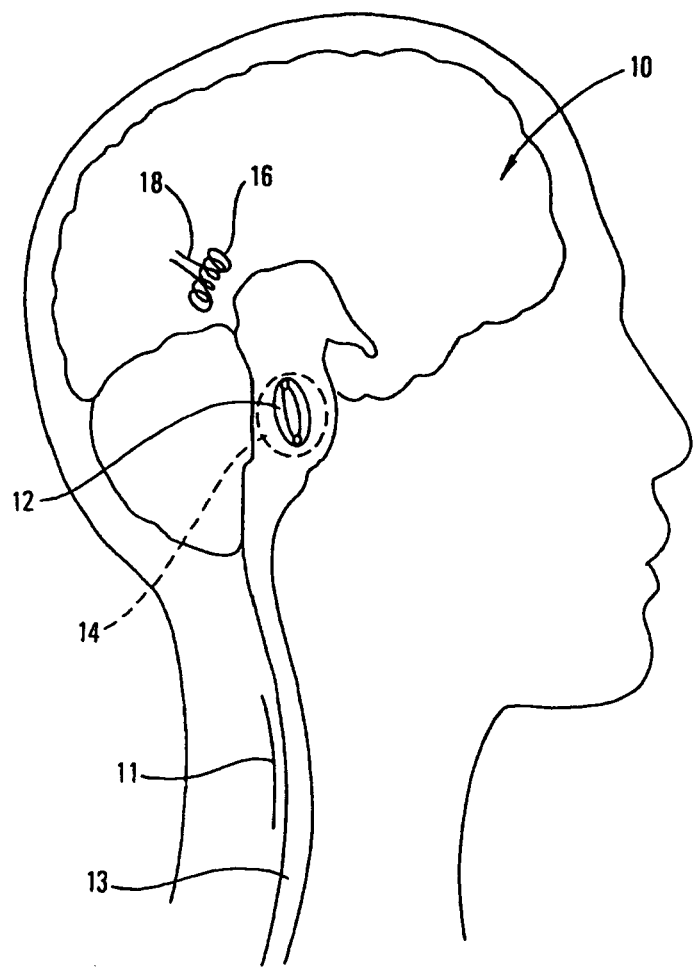
FIG. 1. is a schematic diagram of the head showing mechanical stress devices implanted within brain tissue.

FIG. 1 is a schematic diagram showing several possible locations and geometries for the mechanical stress device (MSD) within the brain 10. A multi-element splined MSD 12 is positioned proximate to the thalamus 14. In this case, the treatment is for Parkinson's disease. A coil MSD 16 is positioned proximate to the trigeminal nerve 18 for treatment of trigeminal neuralgia. A wire form MSD 11 is positioned adjacent to the spinal cord 13.

Figure 2:
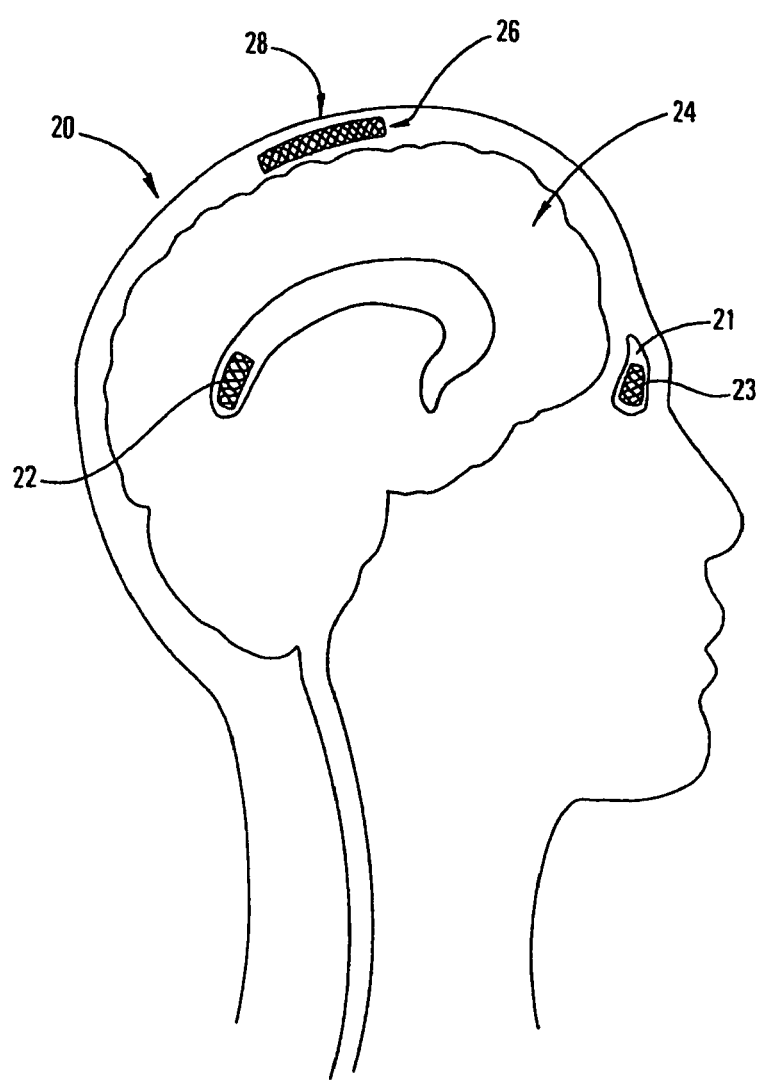
FIG. 2. is a schematic diagram of the head showing mechanical stress devices implanted in the frontal sinus, lateral ventricle of brain, and between the skull and brain tissue.

FIG. 2. is a schematic diagram of the head showing 20 various locations of MSDs of a tubular mesh form. An MSD 22 is located in the lateral ventricle of the brain 24. Another MSD 26 is positioned between the skull 28 and the brain 24. Within the frontal sinus 21 an MSD 23 is positioned. To one skilled in the art, it is obvious that this inventive form of MSD in the nasal sinuses can be to treat symptoms of sinusitis, maintain passageways, treat deviated septums and other nasal sinus ailments. The previously discussed balloon form of MSD can provide an alternative or additional form of therapy within the same sinus treatment realm. In addition, heart rhythms may be affected by proper placement of an MSD within the nasal sinus.

Figure 3:
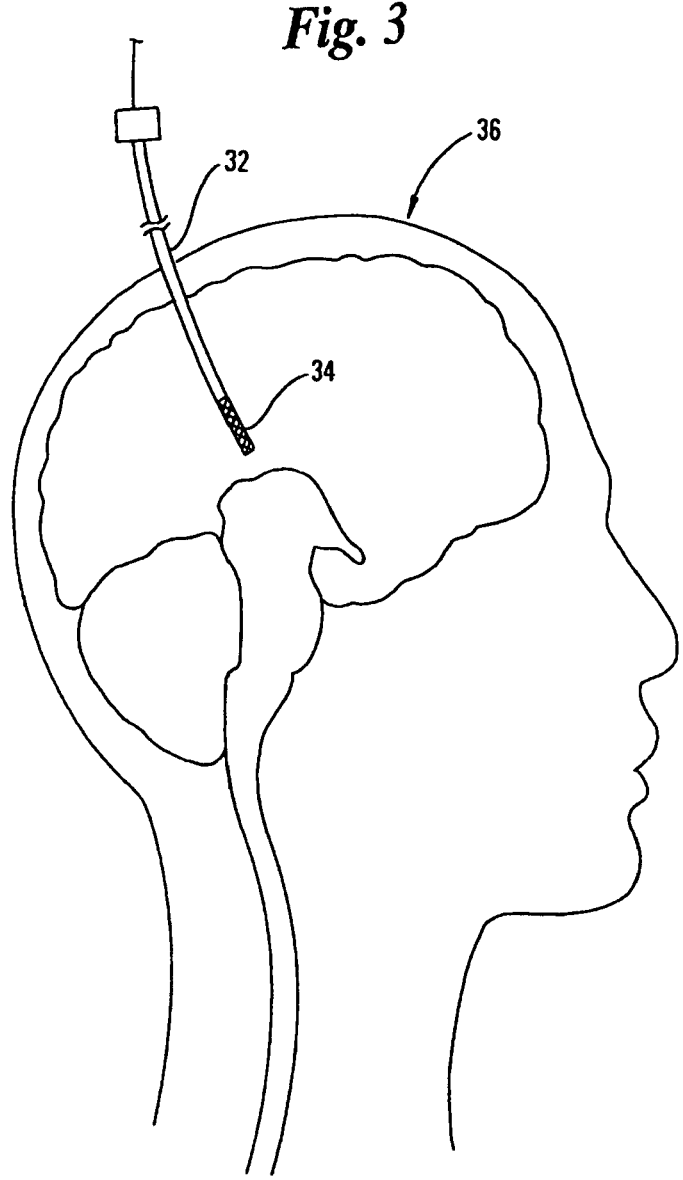
FIG. 3. is a schematic diagram of the head showing the mechanical stress device delivery system.
Figure 4:
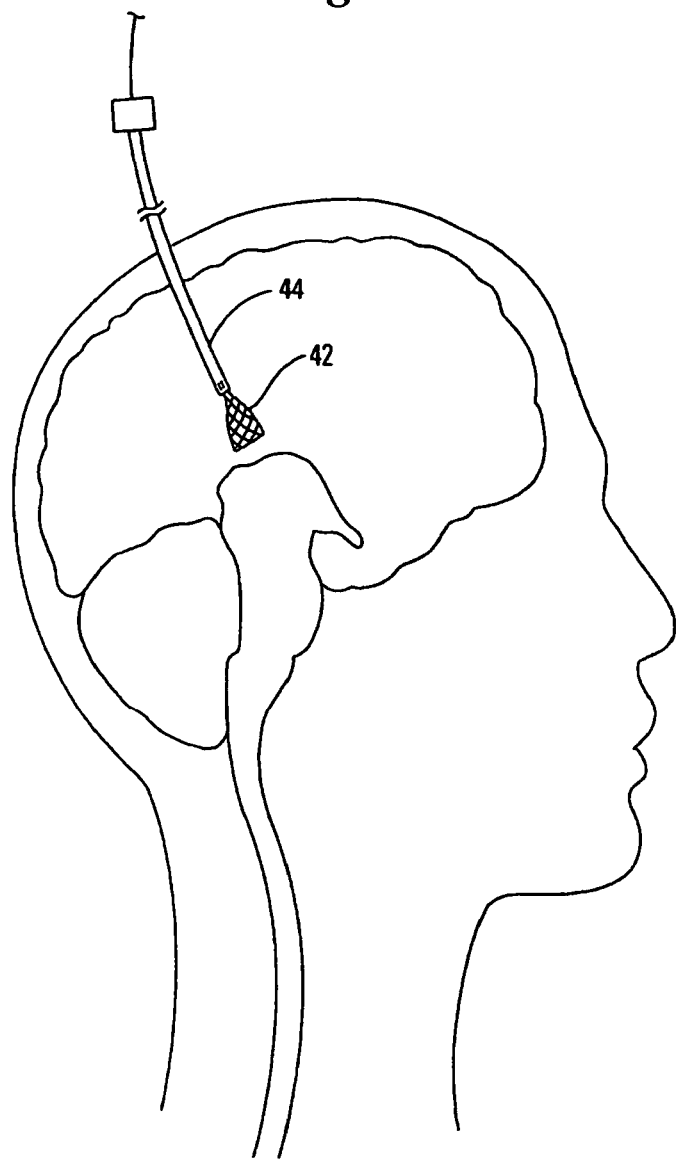
FIG. 4. is a schematic diagram of the head showing the mechanical stress device delivery system.

FIG. 3 and FIG. 4 should be considered together. Together the two figures show the deployment of an MSD.

FIG. 3 is a schematic diagram of a tubular mesh type MSD delivery system. The tubular catheter 32 delivers the tubular mesh MSD 34. The first stage of implantation is navigation of the device to the selected site through the skull 36.

FIG. 4 shows the tubular mesh 42 expanding into position as it emerges from the lumen of the delivery catheter 44. In the self-expanding case, the tubular mesh has a predetermined maximum expandable diameter. The mesh can be made of a shape-memory material such as Nitinol so that when subjected to body temperature the structure expands. With shape memory materials, the shape of the expanded device can be predetermined. Additionally, the device can be retrieved, repositioned, or removed by using its shape memory characteristics. In general the MSD may be used acutely or chronically depending on the disease state of the patient.

Figure 5:
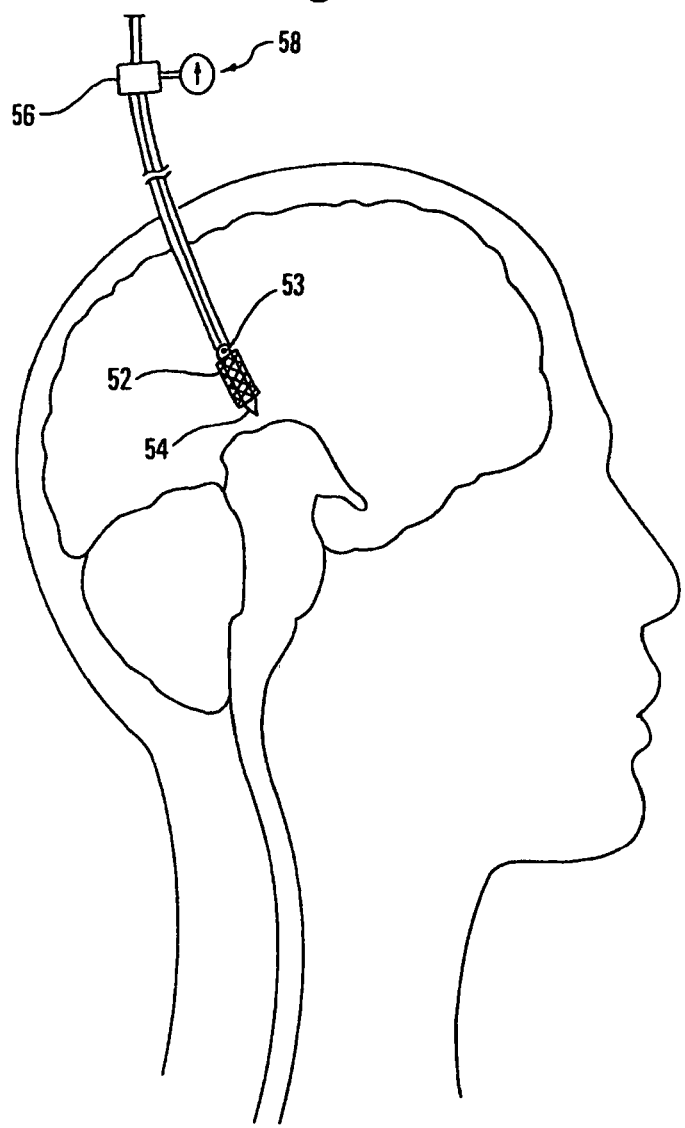
FIG. 5. is a schematic diagram of the head showing the mechanical stress device delivery system.

FIG. 5 shows an alternate balloon expanded MSD 52. In this alternate embodiment a balloon 54 may be used to expand the device within or proximate to selected tissues. In the balloon expandable case, the balloon may have a predetermined minimum or maximum diameter. In addition, the balloon shape can be made to provide proper placement and conformance of the device based on anatomical requirements and location. The balloon may be covered with electrically conductive material. The balloon may be inflated via a syringe 56 and a pressure gauge 58. For example an electrode site 53 may be connected to a remote pulse generator (not shown) to stimulate or ablate the site. The stimulator may activate the electrode either chronically or acutely.

Figure 6:
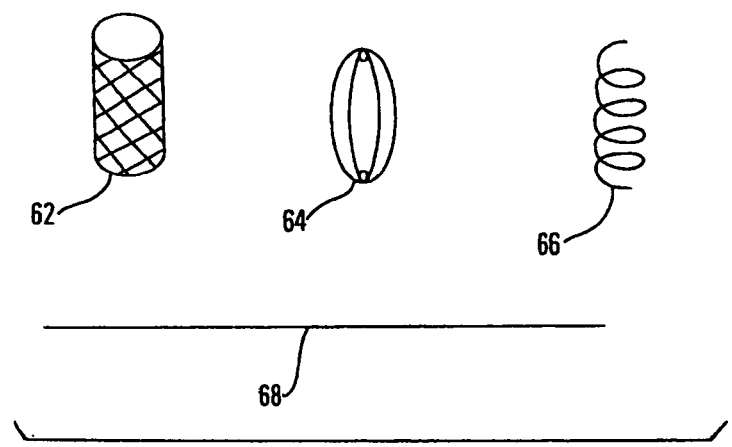
FIG. 6. shows a variety of MSD designs.

FIG. 6 shows a variety of possible MSD shapes and geometries. A tubular mesh 62, a multi-element spline 64, a coil 66, a wire 68 are all acceptable shapes for the MSD although each shape may be specifically adapted to a particular disease state. Other anticipated geometries include clam shells, spherical shapes, conical shapes, screws, and rivets. Although the preferred embodiments consider expandable geometries, alternate geometries can be constructed that retract, compress, collapse, crimp, contract, pinch, squeeze or elongate biologic and physiologic tissues as long as they provide one or more of the desired mechanical, electrical or chemical effects on the selected tissue. Delivery methods for the different possible geometries are anticipated, too.

Figure 7:
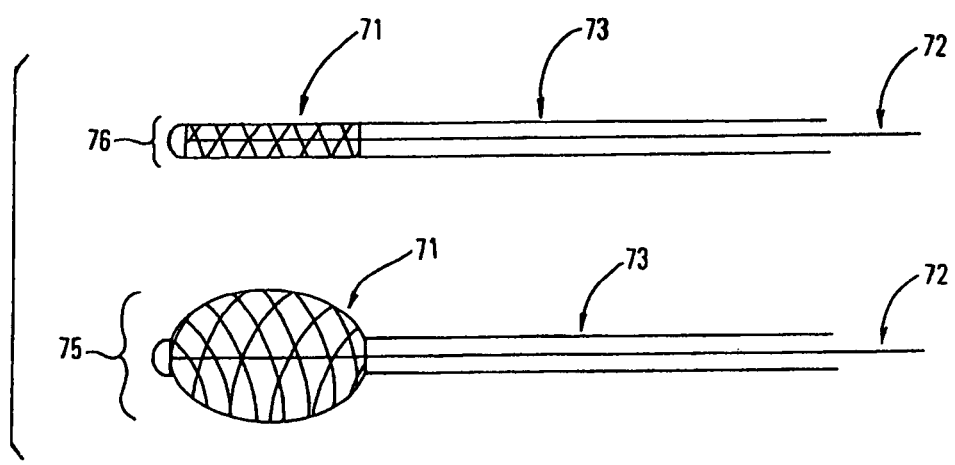
FIG. 7. depicts an MSD, which is manually expanded contracted.

FIG. 7 shows two states of a manually expandable MSD device 71. The device consists of a coaxial shaft 72 and tube 73 arrangement. Attached to the distal end of the shaft 72 and the tube 73 is a braided mesh tube MSD 71. When the shaft 72 and tube 73 are moved opposite of the other by manipulating the proximal ends, the MSD 71 expands 75 or contracts 76. In this case, the MSD 71 can be made of any structure that expands and contracts such as a coil, splined-elements, etc. The various methods of expanding and contracting these structures are, but not limited to, push-pull, rotation, and balloon manipulation. In this type of device, direct connection to either an electrical generator, laser, or monitoring system can be made. In addition, it be envisioned that a device of similar nature be connected to a mechanical energy source, such as rotational or vibrational, in order to increase localized stresses.

The MSD can also utilize devices such as a balloon catheter, expanding devices, or wedges that impart stress or certain levels of localized trauma to selected tissues. The resultant stress and trauma affect the tissues so that current conduction in modified. It is envisioned that any of these devices can be used alone or in conjunction with other treatment modalities in order to provide the desired therapeutic result.

Figure 8:
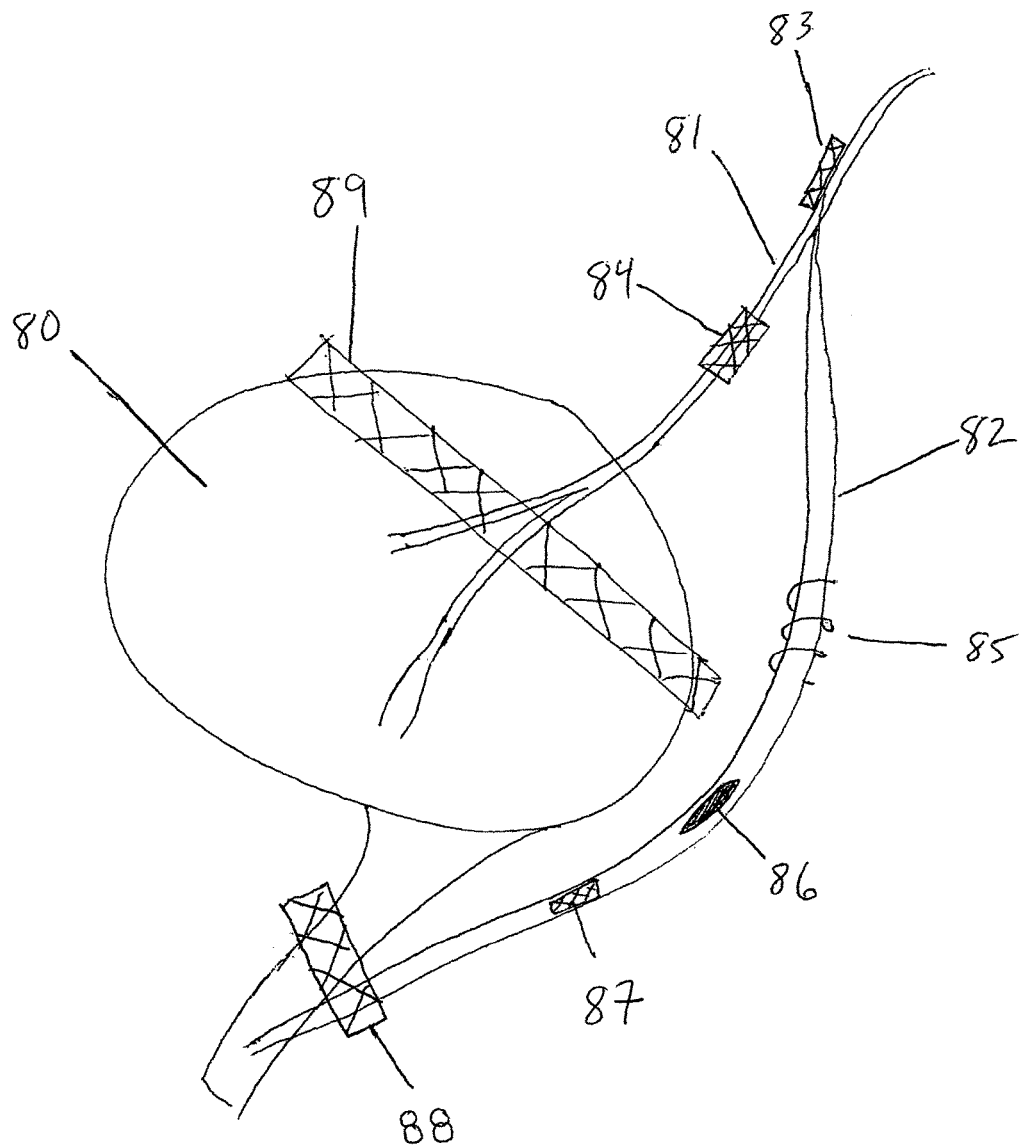
FIG. 8. depicts various MSD designs affecting the nerves of the urinary bladder.

FIG. 8 show a diagram of the urinary bladder 80, its major nerves, and various designs of MSD's in place. The sacral nerve 81 and pudendal nerve 82 are shown being treated with various MSD devices. MSD 83 is placed adjacent to the sacral nerve. MSD 84 is a substantially tubular device that is placed around the sacral nerve and impinges on it as it retracts in diameter. MSD 85 is a coiled structure that is placed around the pudendal nerve and can retract onto the nerve as well act an electrical inductor and receive RF energy from an external source. MSD 86 is a solid structure that is inserted within the pudendal nerve bundle. Like other MSD designs, this type of structure can be injected within the nerve bundle for a more direct impact. Like other MSD embodiments, it can be permanent or biodegradable. MSD 87 is an expandable form of design that is inserted within the nerve bundle. MSD 88 is a form that is wrapped or place around the urethra and pudendal nerve. It can simultaneously treat urge and can also be used to support the urethra to treat other types or incontinence such as stress incontinence. MSD 89, in its implanted state, is a substantially tubular device that contracts and affects the external innervation of the bladder. It can also be activated by internal or external energy sources. A similar type of geometry can be placed within the bladder and affects the bladder innervation as it expands against the internal bladder wall.

Figure 9:
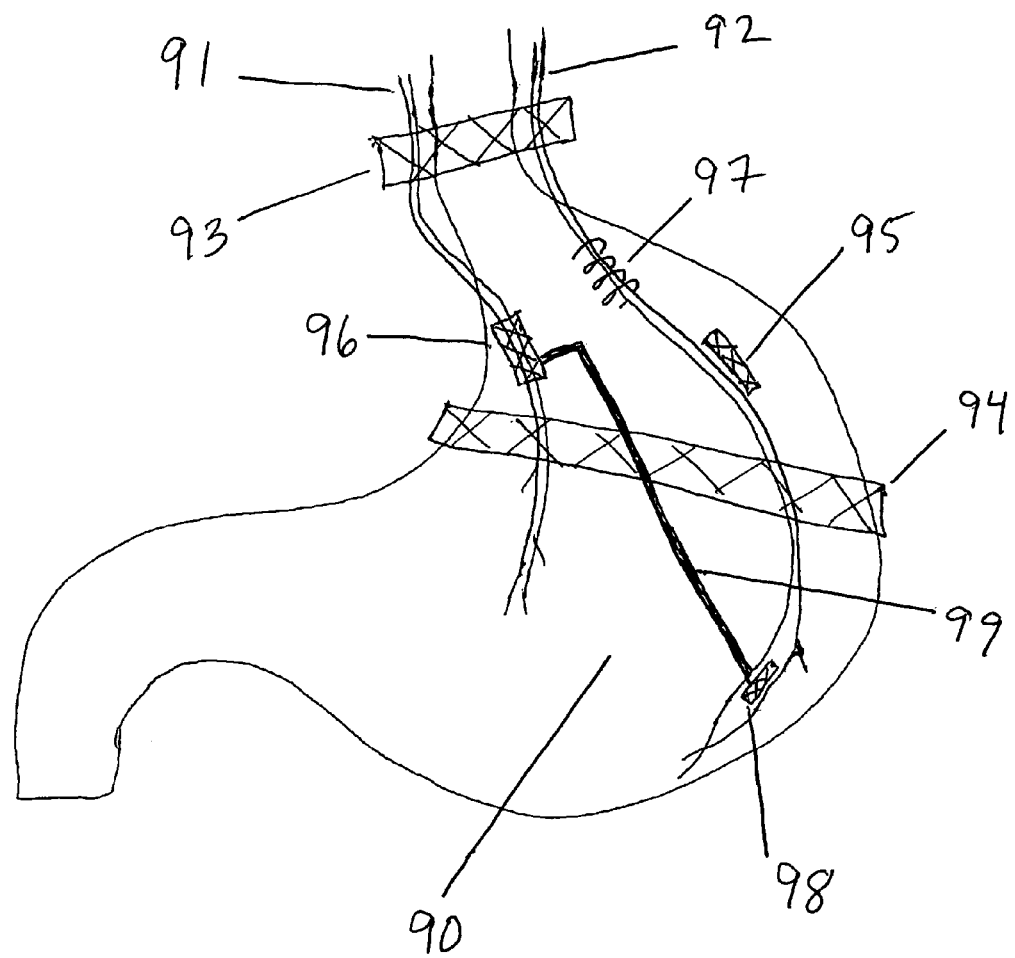
FIG. 9. depicts various MSD designs affecting the nerves of the stomach.

In FIG. 9, the stomach 90 is shown at the junction with the esophagus with its major vagal innervation; anterior vagal nerve bundle 91 and posterior vagal nerve bundle 92. MSD 93 is placed around the stomach 90 and the nerve bundles (91 and 92) affecting the nerve conduction or providing satiety, or both. Similar results are gained by MSD 94 which impinges on the stomach innervation and causes a mechanosensory affect with mechanical forces that modifies the nerve conduction between the stomach and brain. This mechanical affect blocks or reduces the intensity of the "hunger signal" or creates the sense of satiety. A structure similar to 94, albeit in an expanding state, can be placed within the stomach or other portions of the digestive tract in order to therapeutically impact the digestive tracts innervation and sensory pathways. MSD 95 is placed adjacent to a nerve bundle and projects mechanical forces affecting nerve conduction. MSD 96 is a contracting tubular device place around a nerve bundle that creates a nerve block as it impinges on the nerve bundle. MSD 97 is a tubular coil structure placed around the nerve bundle and, similar to MSD 85, can interact with RF energy sources. MSD 98 is placed within the nerve bundle. An electrical connection 99 is shown between MSD 96 and MSD 98. This is illustrative of the ability to use multiple and various MSD's designs in a treatment regimen, as well as to exploit a benefit by electrically interconnecting them.

Figure 10:
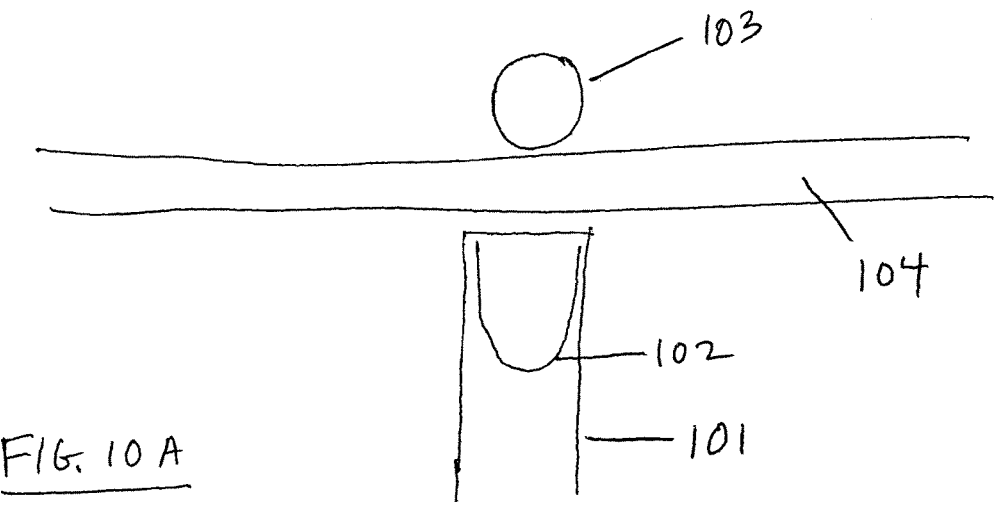
FIGS. 10A, 10B, and 10C shows an MSD being advanced through the wall of an organ and around a nerve on the organ.
Figure 10:
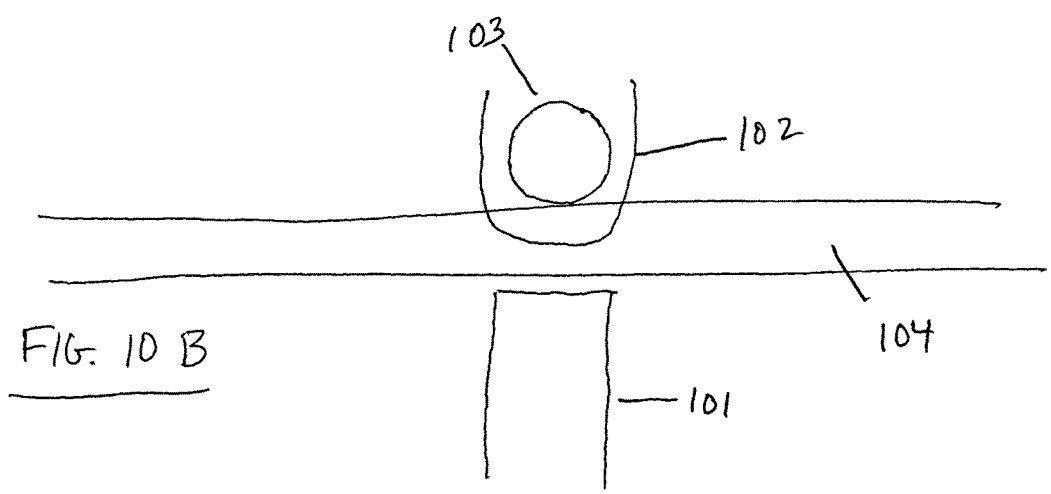
Figure 10:
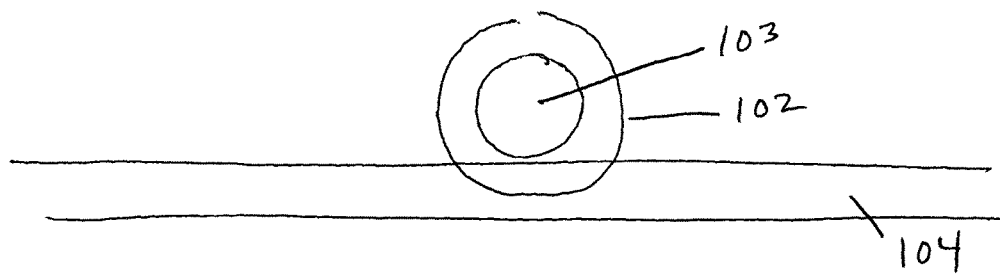

FIGS. 10A, 10B, and 10C shows a sequence of placing an MSD device around a nerve bundle on the surface of an organ. FIG. 10A shows a delivery device 101 loaded with an MSD 102. The delivery device has been advanced to either the internal or external wall of the organ 104. Nerve bundle 103 is located on the opposite side of the organ wall 104. In FIG. 10B, MSD 102 has been pushed out of the delivery device 101, through the organ wall 104 and around the nerve 103. FIG. 10B shows MSD 102 wrapped around the nerve bundle 103 and partially imbedded within the organ wall. In an alternative embodiment, the MSD 102 can also maintain a portion of itself on the wall surface of introduction. The MSD 102 can be made of a preformed material that takes it shape from its inherent elastic or spring properties. Likewise, it can take its shape by utilizing shape memory materials or by mechanical deformation. As previously mentioned, the MSD 102 may also be in the form of a suture, a solid device such as MSD 86, or other MSD designs previously discussed or anticipated. In a slight modification to this embodiment, instead of being advanced through the organ wall 104 and around the nerve bundle 103, the MSD 102 can be installed directly around the nerve bundle 103 from the nerve bundle side of the organ wall 104.

Figure 11:
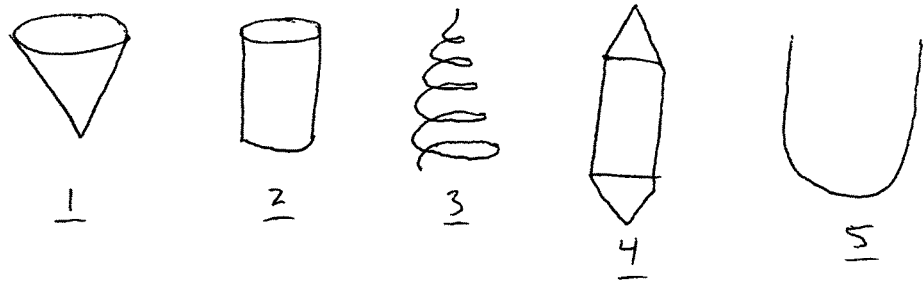
FIG. 11. shows a variety of additional MSD designs.
Figure 11:
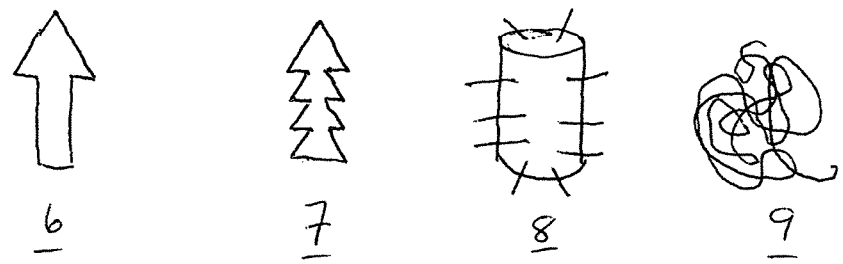
Figure 11:
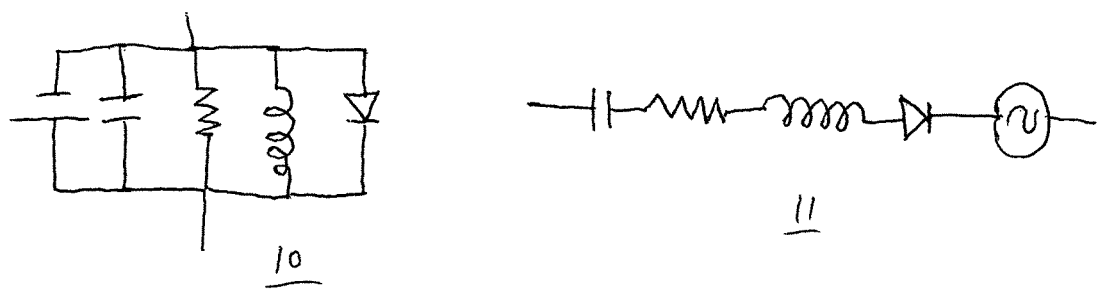
Figure 11:
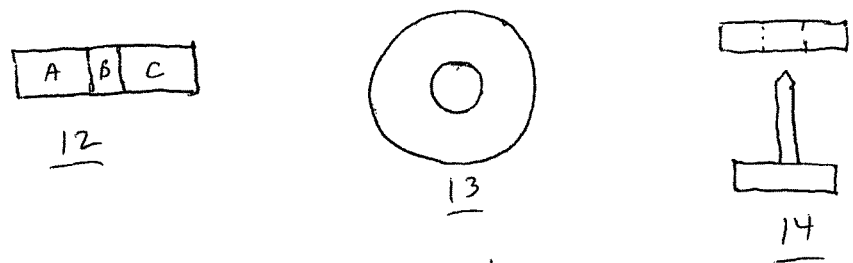

FIG. 11 shows a variety of MSD designs including a cone (1), cylinder (2), screw (3), pointed rod (4), U-clamp (5), dart (6), tined rod (7), cylinder with bristles (8), random coil (9), parallel electrical circuit (10), series electrical circuit (11), multi-segment form (12), round washer form (13), and a 2 piece rivet form (14).

In general, the MSD will have a relaxed or minimum energy state. However the device or the implantation procedure should stretch or stress the device so that it applies a persistent force to the tissues to alter conduction in the strained tissues. In this sense the implanted MSD is not in a fully relaxed state after implantation. In some instances the MSD will cause the tissues to yield or tear generating altered conduction.

Preferably, the MSD is delivered in a minimally invasive procedure such via a catheter or other device. X-ray imaging, fluoroscopy, MRI, CAT scan or other visualization means can be incorporated into the procedural method. In general the devices maybe introduced with cannulas, catheters or over guidewires through naturally occurring body lumens or surgically prepared entry sites. It should be apparent that other surgical and non-surgical techniques can be used to place the devices in the target tissue.

It should be apparent that various modifications might be made to the devices and methods by one of ordinary skill in the art, without departing from the scope or spirit of the invention.

In another embodiment, MSD's may also be designed in order to optimize coupling with external sources of electromagnetic energies via inductive or capacitive coupling. These energies can be utilized to electrically activate the MSD in order to impart voltages and currents to tissues to augment the mechanoelectric and or mechanochemical effects of the MSD. The MSD can be designed in such a fashion where it acts similarly to an implanted antenna. Likewise, the MSD may function primarily as an antenna with little, if any, mechanoelectric effects. The coupled electrical energy to this MSD antenna can be directly imparted to the tissues adjacent to the implanted. The received energy may be used to charge a circuit that is integrated into the MSD structure that discharges at a certain level, directing electrical energy to the desired or adjacent tissue. For example, the circuit may consist of resistors, capacitors, inductors, waveguides, amplifiers, diodes or other components that assist in producing the desired function and effects. The circuit may consist of separate nodes for input and output voltages or it may have one node for both input and output. The MSD may also have a discrete antenna, antenna-circuitry or waveguide for receiving or transmitting energy and/or information.

In another embodiment, the MSD may consist of circuitry that can automatically treat the neurological defects by utilizing the electrical energy generated by the physiologic tissues in which the MSD is implanted. In the case of epilepsy, focal tissues generate errant currents that result in seizure activity. These affected focal tissues are readily identified with standard CAT or MRI imaging systems and an MSD can then be implanted into these tissues. When the errant currents are generated, these currents charge the circuitry in the MSD. When the circuitry is charged to a predetermined level, it discharges back into the affected focal tissues and resolves the errant currents. A RC time constant circuit can be utilized for this MSD version. Amplifiers, signal generators and other processing circuitry can be incorporated into an MSD in order to increase or modify the output.

In another embodiment, the MSD has a covering to increase the surface area of the device. The covering can encompass the entire device or selected portions and can be positioned on the outside or inside surface. Such a covering can be made of polymers such as Teflon, polyethylene, polyurethane, nylon, biodegradable materials or other polymeric materials. The covering can also be made of a fine metal or polymeric mesh. In all cases, the covering can be bonded to the surface of the MSD or applied as a loose sheath-type covering. The covering can have therapeutic materials applied or incorporated into the covering material itself. Examples of the therapeutic materials include drugs, stem cells, heparin, biologic materials, biodegradable compounds, collagen, electrolytes, radiopaque compounds, radioactive compounds, radiation-activated substances, or other materials that enhance the clinical effects and/or procedures.

In another embodiment, the MSD may have a material that substantially fills its interior space. Such a material would prevent formation of spaces or voids once an expandable MSD is placed. The materials may be fibrous, gels, porous, foam or sponge-like and may be incorporated with polymers, glass, metals, radioactive compounds, biologic tissues, drugs, or other suitable materials that may enhance clinical effective and/or procedures. The materials would be flexible enough to allow expansion of the MSD and can be made of polymers, glass, metal, biologic tissues, drugs, or other suitable materials. Although not limited to, examples of biologic materials include stem cells, brain cells and matter, thalamic tissues, and collagen.

The use of appropriate materials may also provide certain electrical properties to the MSD that enable it to receive, store and/or transmit electrical energy. The dielectric properties of these materials would provide electrical capacitor properties and function to the MSD. This provides the benefit of creating an electrical circuit that can receive, store and discharge energy from various sources. The source may be external generators that couple capacitively, inductively or magnetically, RF energy from a predetermined portion of the electromagnetic spectrum to the MSD. In addition, the source may be an electrical generator connected by a wire or a cable to the MSD.

Another means of generating therapeutic electrical energy is to utilize galvanic effects. Proper material selection and interaction with physiologic fluids and tissues would result in galvanic currents or electrochemical reactions being generated by the MSD. Generally, dissimilar metals or materials would be used in order to optimize the generation of galvanic currents. These currents could provide constant therapeutic electrical energy levels to the desired tissues. This could potentially benefit patients suffering from Parkinson's, epilepsy, pain, depression, migraines, etc. The galvanic currents can also be used to energize, activate, or charge circuits or batteries that provide monitoring, diagnostic or therapeutic effects. This technology could also be used for intravascular devices such as stents in order to prevent thrombosis or hyperplasia or to energize implantable sensors or monitoring devices. Galvanic devices can also be used to treat peripheral pain, generate revascularization of myocardial tissues, treat tumors, provide electrical potential for drug transport into tissues, treat endometriosis, or to power, energize, activate, operate or charge other medical devices such as cardiac pacemakers, defibrillators or other electrical generator based systems.

In another embodiment, the MSD may be a structure that completely or partially slices into tissue. The slicing action cleaves or separates the tissue physically breaking the electrical conduction paths. In this case, the MSD can reach complete or partial state of expansion. In the case of complete expansion, the residual stress to the tissue would be approaching zero, while the partial expansion would result in a combined clinical effect via part mechanical stress and part slicing of tissue.

Additional methods of constructing MSD's include using three-dimensional structures such as wedges, slugs, clips, rivets, balls, screws, and other structures that impart stress to the tissues. Materials such as open-cell polymers, gels, liquids, adhesives, foams can also be inserted or injected into tissue and tissue spaces in order to generate the desired amount of stress. These types of material could also have the additional benefit of being therapeutic agents or carriers for therapeutic agents.

Another MSD structure can consist of a balloon that is positioned at desired location, inflated within the tissue, and then detached and left in an inflated state. Examples of inflation media can be fluids, gels, foams, pharmaceuticals, and curable resins.

Other embodiments of MSD composition include construction using magnet and magnetic materials that complement the localized effects of the MSD by controlling the electrical properties of the tissues using gradients and fields. In the case where the MSD is composed of magnet materials, the magnetic field emanating from the magnetic materials would bias electric fields within the tissues. This effect can control the direction of current conduction within the tissues. In the case where the MSD is composed of magnetic materials that interact with magnetic gradients and fields, an external magnet placed proximate to the head can physically manipulate the MSD. Movement of the magnetic would cause movement of the MSD. The manipulation would result in dynamic stresses to the tissues adjacent to the MSD, thus affecting the electrical properties of the tissues and potentially resolving seizures or tremors.

Other MSD can be built with an integrated circuit consisting of a resistor, capacitor, and an inductor. The inductor couples with the external electromagnetic energy and the resulting current generated in the inductor charges the capacitor. Based on the RC time constant of the circuit, the capacitor charges to a certain level and then discharges directly to the desired tissues and the errant currents are disrupted by this discharge. A combination of electromagnetic coupling and direct connection incorporates a generator with a transmission coil and a ground connection made directly to the patient, providing a closed-loop circuit. The ground connection can be made directly to the skin of the patient using a clip or a grounding pad such as used during electrosurgical procedures. The pad may be applied to the patient with tape, bands or adhesives. The ground connection may also be implanted on or within tissue. External generators may be manually operated by the patient or other person or may be automatically operated utilizing monitoring systems that identify seizures or tremors and energize the MSD. Likewise, automatic circuitry such as the aforementioned RC-timing circuit can be used. The generators may also be programmed to energize at a certain predetermined sequence, rate and level. In the treatment of mania, depression, schizophrenia or similar disorders, the generator may provide a constant output to maintain a consistent state of electrical condition of the tissues. For convenience, the external generators may be attached directly to the head or incorporated into a hat, helmet, or band. Alternately, the transmission coil separately may be attached directly to the head or incorporated into a hat, helmet, scarf or band. The coil may encompass the entire head or specific portions in order to attain desired coupling with the MSD. In addition, strain gauge technology can be incorporated that can measure and correlate the amount of mechanical stress and strain imparted to tissues or stress and strains imparted to the device by tissues and active organs such as vessels, hearts, valves, and other organs and tissues. Such data can be used to provide a feedback means by which to control the MSD in order to provide treatment as necessary based on the physiologic response or activation.

Likewise, as mentioned previously, the electrical energy inherent in physiologic tissue may also be the source that energizes the circuit. Again, it should be noted that various modifications might be made to the devices and methods by one of ordinary skill in the art, without departing from the scope of the invention.

What is claimed:

1. A method for treating obesity comprising:
   surgically accessing a vagal nerve on a stomach;
   positioning a mechanical device proximate to the vagal nerve on the exterior of the stomach with a delivery device;
   detaching the mechanical device from a delivery device by unscrewing the mechanical device from the delivery device; and
   applying a mechanical force to the vagal nerve directly with the mechanical device to modify vagal nerve conduction.

2. The method of claim 1, wherein the mechanical device is biodegradable.

3. The method of claim 1, wherein the mechanical device is placed by a laproscopic surgical procedure.

4. The method of claim 1, wherein the mechanical device is an adjustable balloon.

5. The method of claim 1, wherein the mechanical device is energized by an electrical generator.

6. The method of claim 1, wherein the mechanical device is an injectable substance.

7. The method of claim 1, wherein the mechanical device is introduced from within the stomach.

8. The method of claim 1, wherein the mechanical force is expansion.

9. The method of claim 1, wherein the mechanical force is contraction.

10. The method of claim 1, wherein the mechanical device is permanently implanted.

11. The method of claim 1, wherein the mechanical device is temporarily implanted and later removed.

12. A method for treating obesity comprising:
    surgically accessing a vagal nerve on a stomach;
    positioning a mechanical device proximate to the vagal nerve on the exterior of the stomach with a delivery device;
    detaching the mechanical device from a delivery device by detaching the mechanical device from the delivery device with a detent release; and
    applying a mechanical force to the vagal nerve directly with the mechanical device to modify vagal nerve conduction.

* * * * *